United States Patent [19]

Johnson

[11] 4,032,579

[45] June 28, 1977

[54] 11-SUBSTITUTED STEROIDS AND INTERMEDIATES

[75] Inventor: William S. Johnson, Portola Valley, Calif.

[73] Assignee: The Board of Trustees of Leland Stanford Junior University, Stanford, Calif.

[22] Filed: Apr. 28, 1975

[21] Appl. No.: 572,379

[52] U.S. Cl. .................. 260/617 R; 260/631 R; 260/614 R; 260/615 R; 260/348 C; 260/348 A; 260/488 H; 260/486 R; 260/327 M; 260/340.9; 260/340.7; 260/611 R; 260/397.45
[51] Int. Cl.² ........................................ C07C 35/06
[58] Field of Search ........................... 260/617 R

[56] References Cited

UNITED STATES PATENTS 3,741,987  7/1973  Johnson et al. ............... 260/617 R
3,904,698  9/1975  Johnson et al. ............... 260/617 R

OTHER PUBLICATIONS

Johnson et al., J.A.C.S., vol. 93, No. 17, pp. 4332–4334 (1971).

*Primary Examiner*—James O. Thomas, Jr.
*Assistant Examiner*—James H. Reamer
*Attorney, Agent, or Firm*—Townsend and Townsend

[57] ABSTRACT

Precursor compounds are provided for use in the synthesis of 11-chalcogensubstituted steroids and nor-steroids, particularly 18-, 19- and A-nor-steroids. The compounds are acyclic or substituted polyenine with the olefinic groups having the proper geometry to provide the natural ring fusions upon cyclization. To initiate cyclization, a chalcogen atom is positioned in relation to a double bond, so that on protonation of the chalcogen atom, the resulting carbocation will interact with the double bond to form a pi bond if the cyclization initiator is carbocyclic and a sigma bond if the cyclization initiator is acyclic. Upon cyclization, it is found that the substituent at C-11 of the resulting steroid is in the alpha position. Various methods are provided for producing the cyclization precursor.

1 Claim, No Drawings

11-SUBSTITUTED STEROIDS AND INTERMEDIATES

The invention described herein was made in the course of work under a grant or award from the Department of Health, Education, and Welfare.

BACKGROUND OF THE INVENTION

Field of the Invention

The primary starting material for commercially employed steroids are plant steroids. Since the plant steroids differ as to substituents on the ring and particularly as to the substituent at the C-17 position, substantial modification of the plant steroid is required. In addition, because one is concerned with a product which is susceptible to fluctuation and availability, there have been substantial efforts to find alternative means for preparing steroidal compounds.

In synthesizing steroids from small readily available organic fragments, one must be concerned with the complex structure of the polycyclic steroid, as well as the particular geometry of the substituents and the ring fusions. In synthesizing a steroid, it is therefore necessary that one introduce the various substituents having the desired geometry and in preparing the rings, provide a means for obtaining the ring fusions having the specified geometry. Since the synthesis will invariably involve a number of steps, it is necessary during the synthetic sequence to insure that subsequent steps do not affect prior conformations which have been introduced so as to provide desired geometry. In addition, where catalyzed cyclization of a polyunsaturated compound is involved there must be concern about the effect of various substituents on the carbon atoms which will ultimately be annular carbon atoms. Since the cyclized compound will be more compact then the acyclic compound, non-bonded steric interactions can be expected to deleteriously affect the course of the cyclization. Where heteroatoms are present on the polyunsaturated chain, the inductive effect of the heteroatoms, their interaction with acid, and their ultimate geometry must be taken into account. In addition, the choice of the polyunsaturated compound must allow for cyclization to the steroidal structure without interruption, so that the tetracyclic compound is formed, rather than a lower order polycyclic compound.

SUMMARY OF THE INVENTION

Novel cyclization precursor compounds are provided which are substituted with functionalized substituents at a carbon atom which serves as the C-11 position. The compounds are acyclic or substituted monocyclic compounds which are polyunsaturated. The C-11 carbon atom is substituted with a chalcoxy substituent. The cyclization precursor has a group which serves as an initiator of the cyclization upon acid catalysis, which has a chalcogen atom (oxygen or sulfur) in juxtaposition with a double bond, so that upon protonation of the chalcogen atom, there is interaction with the carbocation and double bond to form a new carbon-carbon bond. Methods are provided for preparing the cyclization precursor.

DESCRIPTION OF THE SPECIFIC EMBODIMENTS

In accordance with this invention, there are provided: intermediates for cyclization to steroidal or norsteroidal structures; means for preparing the intermediates; and means for cyclizing polyenyne intermediates to a tetracyclic steroidal structure, which may then be further modified as desired to provide the desired steroid. The intermediates are such as to provide a polyenyne which had a chalcoxy group at the carbon atom which will ultimately provide the C-11 position of the steroid. The substituted polyenynes are capable of being cyclized to the desired steroid without loss of the chalcoxy group.

The description of the invention will be divided up as follows:

I. Intermediates
II. Methods of Preparing Intermediates
III. Cyclization
IV. Tetracyclic Products The description of the above categories will be followed by the experimental section.

Before considering the individual categories, the following chart is provided which shows the major fragments employed for building the intermediate or precursor to the steroid structure which is then employed for cyclization to the steroids. The synthesis is predicated upon the use of two fragments which are condensed to a polyenyne structure having the proper geometry about the sites of unsaturation, so that on cyclization, the product obtained has the naturally occurring ring fusions.

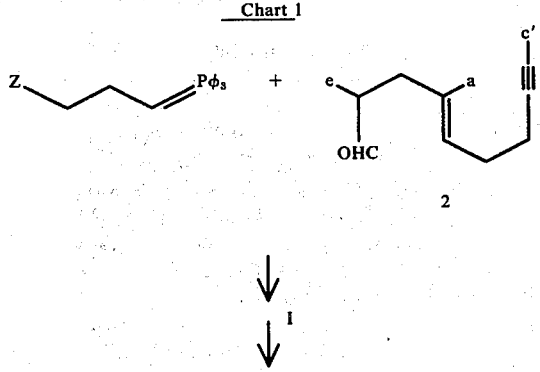

Chart 1

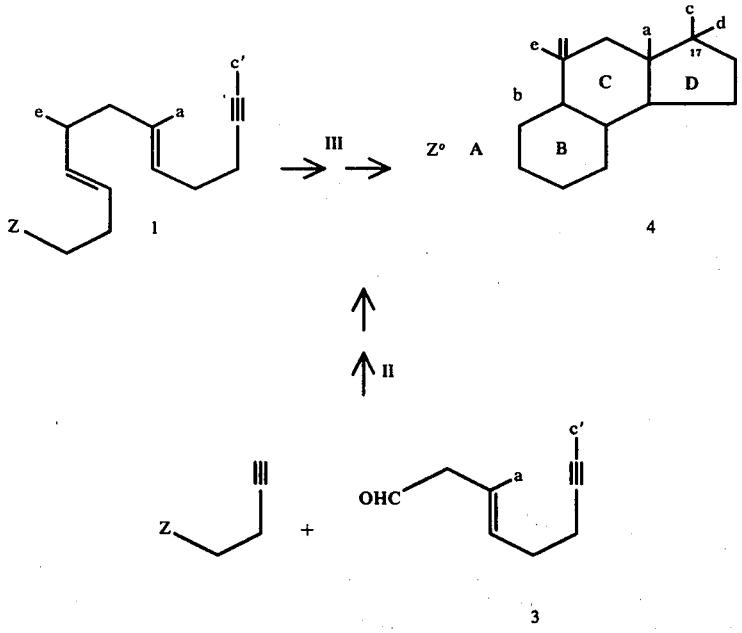

The small letters indicate substituents on the basic ring structure. Z is an initiator group which will be discussed in detail subsequently. Z° intends the residue of the A ring, which may have the annular carbon atoms substituted or unsubstituted and there may be one or more sites of ethylenic unsaturation.

In the cyclization, the intermediate is cyclized with an acid catalyst in combination with a nucleophile. The intermediate may be divided into three parts: (1) initiator (Z); (2) diene linking group (Y); and (3) terminator (X). This molecule (Z—Y—X) is reacted with the nucleophile (WH) under acidic conditions to provide the steroid structure.

The initiator will be cyclic or acyclic and will having the following functionality as part of its structure:

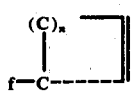

wherein:
n is of from 2 to 3, being 3 when the broken line is not a bond;
f is a substituent bonded to the carbon atom by a chalcogen atom of atomic number 8 to 16 (oxygen or sulfur); and
the broken line indicates the presence of a bond when Z is cyclic and the absence of a bond when Z is acyclic.
The initiator has an allylic chalcogen atom when cyclic and a C-6 chalcogen atom to a Δ¹ double bond when acyclic.

The linking group (Y) is a 5-substituteddeca-3,7-dien-1,10-ylene, which may be further substituted at the 7-position by a lower alkyl group (1–4 carbon atoms), particularly straight chained. The substituent at the 5-position, which will ultimately be the 11-position of the steroid, will be functionalized by being bonded to the annular carbon atom through chalcogen.

The terminator (X) is an alkinyl or substituted alkinyl group of from 2 to 12 carbon atoms, more usually of from 3 to 10 carbon atoms, wherein the terminal acetylenic carbon atom may be substituted with a hydrocarbyl group (hydrocarbyl intends a group composed solely of carbon and hydrogen which is aliphatic, alicyclic, aromatic or combinations thereof, particularly free of aliphatic unsaturation) and substituted hydrocarbyl, particularly substituted through chalcogen (O and S).

Finally, the nucleophile (WH) will react with the positive charge developed at the acetylene group to form a covalent bond. The nucleophile may be retained in the workup of the cyclic product or may be modified by virtue of the workup conditions, so that the original product is not isolated.

I. Intermediates

The cyclization precursor is a trienine having at least one chalcogen atom, generally not more than 5 chalcogen atoms, usually 1 to 4 chalcogen atoms, more usually 1 to 3 chalcogen atoms. The intermediates will have at least 19 carbon atoms, and generally not more than 50 carbon atoms, usually not more than 40 carbon atoms, and more usually having from about 19 to 36 carbon atoms, preferably from about 19 to 30 carbon atoms.

(The term "chalcoxy," when used in this disclosure, shall mean hydroxy, mercapto, oxyether, thioether, but shall not include esters, peroxides, and higher oxidation states of sulfur, e.g. sulfoxide.)

For the most part, the cyclization precursors will have the following formula:

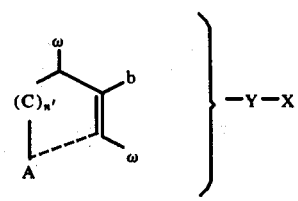

wherein:

one of the omegas (ω) is a bond to —Y—X and is otherwise hydrogen;

b is hydrogen or alkyl of from 1 to 4 carbon atoms, more usually of from 1 to 2 carbon atoms, and usually straight chained;

n' is an integer of from 1 to 2;

A is an alkyl or alkylidene radical (depending on whether the broken line is a bond) of from 1 to 12 carbon atoms, more usually of from 1 to 7 carbon atoms having from 1 to 2 alpha-chalcoxy groups bonded to the carbon atom in the chain and may have an oxygen atom bridging to the adjacent saturated carbon atom to form an epoxide; and the broken line indicates the presence or absence of a bond, depending upon whether the initiator is cyclic or acyclic.

Y is of from 10 to 20, usually 10 to 18, preferably 10 to 12 carbon atoms, and has the skeletal structure 3,7decadien-1,10-ylene, and is substituted at the 5-position with a chalcoxy group of from 0 to 12, usually 0 to 8 carbon atoms; and X is a 1-hydrocarbinyl group, e.g. 1-alkinyl, phenylethinyl, etc. of from 2 to 12, usually 2 to 8, preferably 2 to 6 carbon atoms having from 0 to 1 chalcoxy or carboxyester groups, particularly oxy groups (including carboxy ester) of from 0 to 7, usually 0 to 4 carbon atoms.

The carbon atoms in the parenthesis may be substituted or unsubstituted, when substituted being substituted with alkylidene of from 1 to 4 carbon atoms, more usually of from 1 to 3 carbon atoms, or chalcoxy of from 0 to 6 carbon atoms, more usually of from 0 to 4 carbon atoms, and wherein 2 chalcoxy groups bonded to the same carbon atom may be taken together to form a cyclic ketal of from 5 to 6 annular members, there being a total of from 0 to 2 substitutents on the carbon atoms in the parenthesis.

More particularly, the precursors to the tetracyclic compounds will have the following formula:

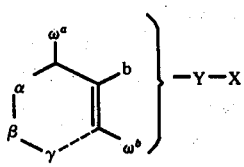

wherein:

the broken line is a bond when the group is cyclic and is not a bond when the group is acyclic;

α is methylene or a bond, being methylene when the broken line is not a bond;

β is alkylidene of from 1 to 8 carbon atoms, usually of from 1 to 6 carbon atoms, more usually of from 1 to 4 carbon atoms having from 0 to 2 alpha-chalcoxy groups, wherein the two chalcoxy groups may be taken together to form a cyclic ketal of from 5 to 6 annular members, and having from 0 to 1 site of ethylenic unsaturation, or with the proviso that the broken line is a bond, of the following formula $\omega^c$—CH<;

γ is alpha-chalcoxyhydrocarbyl having from 1 to 2 alpha-chalcoxy groups and being of from 1 to 10 carbon atoms, more usually of from 1 to 8 carbon atoms and free of aliphatic unsaturation and includes alkyl, cycloalkyl and phenyl substituents on the carbon atom in the chain, and wherein an oxygen atom may bridge to β to form an epoxy group;

when the broken line is a bond, γ is usually alkylidene of from 1 to 6 carbon atoms, more usually of from 1 to 4 carbon atoms and having from 1 to 2 alpha-chalcoxy groups which may be taken together to form a cyclic ketal of from 5 to 6 annular members, and when the broken line is not a bond, γ will be hydrocarbyl having from 1 to 2 alphachalcoxy groups which may be taken together to form a cyclic acetal or ketal of from 5 to 6 annular members and is of from 1 to 8 carbon atoms, more usually of from 2 to 8 carbon atoms and free of aliphatic unsaturation, and wherein one of the chalcoxy groups may be taken together with β to form an epoxide ring;

b is hydrogen or lower alkyl of from 1 to 4 carbon atoms, more usually of from 1 to 3 carbon atoms, and preferably of from 1 to 2 carbon atoms and is straight chained; and $\omega^{a-c}$ is a bond to Y and is otherwise hydrogen;

Y is 5-e-7-a-3,7-decadien-1,10-ylene, where the 1-position is bonded to Z and the 10-position is bonded to X and is of the formula:

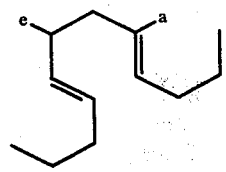

wherein:

a is hydrogen or lower alkyl of from 1 to 4 carbon atoms, usually of from 1 to 3 carbon atoms and preferably of from 1 to 2 carbon atoms, particularly methyl, and usually straight chained;

e is chalcoxy of from 0 to 12 carbon atoms, more usually of from 0 to 10 carbon atoms, and preferably of from 0 to 8 carbon atoms, particularly preferred hydroxy; and X is of the formula:

wherein:

g is hydrogen, hydrocarbyl of from 1 to 10 carbon atoms, chalcoxy hydrocarbyl of from 1 to 10 carbon atoms, or acylcarboxy hydrocarbyl of from 1 to 10 carbons, particularly when aliphatic, lower alkyl of from 1 to 4 carbon atoms, chalcoxy hydrocarbyl, particularly alpha-chalcoxyalkyl of from 1 to 8 carbon atoms, more usually of from 1 to 4 carbon atoms, and particularly hydroxyalkyl of from 1 to 2 carbon atoms, preferably hydroxymethyl, or acylcarboxyalkyl of from 1 to 8 carbon atoms, more usually of from 1 to 4 carbon atoms, more usually of from 1 to 4 carbon atoms, and preferably acetoxymethyl wherein the acyl group is free of unsaturation;

when aromatic, phenyl, alkylphenyl of from 7 to 10 carbon atoms and chalcoxyphenyl of from 6 to 10 carbon atoms.

Illustrative Z groups include:
1-hydroxy-1-ethylcyclopent-2-en-2-yl;
trimethylene dithioketal of 6-hydroxy-5-oxo-2-ethylcyclohex-1-en-1-yl;
2-hydroxy-2-ethylcyclopent-3-en-1-yl;

2,3-butylene ketal of 6-hydroxy-5-oxo-2-methylcyclohex-1-en-1-yl;
6-hydroxy-5-isopropylidenyl-2-methyl-cyclopent-1-en-1-yl;
ethylene dithioketal of 2-ethyl-6-oxocyclohex-1-en-1-yl;
2,3-butylene dithioketal of 2-ethyl-4-oxocyclohex-2-en-1yl; and
2-ethyl-5-hydroxy-5-methylcyclopent-1-en-1-yl.
Illustrative Y groups include:
5-hydroxy-7-ethyldeca-3,7-dien-1,10-ylene;
5-methylthio-7-methyldeca-3,7-dien-1,10-ylene;
5-p-tolylmethoxy-7-ethyldeca-3,7-dien-1,10-ylene;
5-butoxy-7-methyldeca-5,7-dien-1,10-ylene;
5-sec-butoxy-7-ethyldeca-3,7-dien-1,10-ylene; and
5-thiol-7-methyldeca-3,7-dien-1,10-ylene.
Illustrative X groups include:
prop-1-in-1-yl;
3-hydroxyprop-1-in-1-yl;
3-methoxyprop-1-in-1-yl;
3-hydroxybut-1-in-1-yl;
3-ethoxyprop-1-in-1-yl;
3,4-dimethoxybut-1-in-1-yl;
3-benzyloxyprop-1-in-1-yl;
2-phenylethinyl;
2-p-phenetylethinyl; and
2-benzylethinyl.

For the most part, the cyclic compounds of this invention will have the following formula:

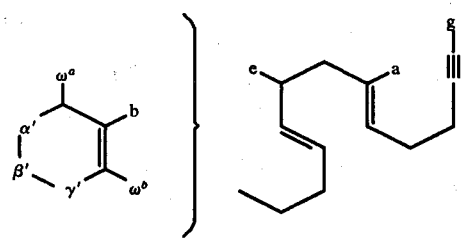

wherein:

$a$ and $b$ are hydrogen or alkyl of from 1 to 4 carbon atoms, more usually of from 1 to 3 carbon atoms, and preferably of from 1 to 2 carbon atoms, particularly methyl, with $a$ preferably being alkyl;

$g$ is alkyl, having from 0 to 1 chalcoxy or acylcarboxy group, i.e. chalcoxyalkyl, or acylcarboxyalkyl, particularly alkyl and oxyalkyl of from 1 to 8 carbon atoms, more usually of from 1 to 6 carbon atoms, preferably of from 1 to 4 carbon atoms, particularly preferred of from 1 to 2 carbon atoms, particularly methyl and hydroxymethyl, or carboxcyclic aryl of from 6 to 12, usually 6 to 10 carbon atoms, having from 0 to 2, usually 0 to 1 chalcoxy substituents or carboxyester substituents;

$e$ is chalcoxy of from 0 to 12 carbon atoms, usually of from 0 to 8 carbon atoms, more usually of from 0 to 4 carbon atoms, and preferably hydroxy;

$\alpha'$ is a bond or methylene;

$\beta'$ is alkylidene of from 1 to 8, more usually of from 1 to 6, and preferably of from 1 to 4 carbon atoms, having from 0 to 2 alpha-chalcoxy groups bonded to the annular carbon atom, wherein 2 chalcoxy groups may be taken together to form a cyclic ketal of from 5 to 6 annular members, and having from 0 to 1 site of ethylenic unsaturation, particularly exo unsaturation, that is, a double bond to the annular carbon atom, or of the formula $\omega^c$—CH<;

$\gamma$ is the alpha-chalcoxyalkylene of from 1 to 8, more usually 1 to 6, and preferably 1 to 4 carbon atoms, having from 1 to 2 chalcoxy groups bonded to the annular carbon atom, wherein 2 chalcoxy groups may be taken together to form a cyclic ketal of from 5 to 6 annular members; and wherein one of $\omega^{a-c}$ is a bond, but are otherwise hydrogen.

When Z is acyclic, the compound for the most part will have the following formula:

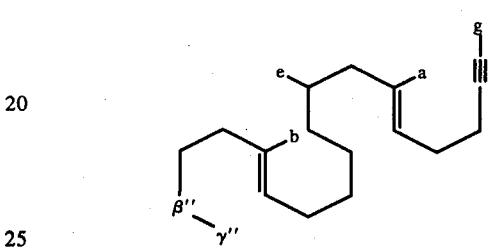

wherein:

$a$, $b$, $e$ and $g$ have been defined previously;

$\beta''$ is an aliphatic hydrocarbylidene group having from 0 to 2 alpha-chalcoxy substituents and from 0 to 1 site of ethylenic unsaturation, particular $\Delta^1$ and is of 1 to 8 carbon atoms, more usually of from 1 to 6 carbon atoms, and preferably of from 1 to 4 carbon atoms, and usually methylene and may be taken together with $\gamma''$ to form an epoxide ring; and $\gamma''$ is chalcoxymethyl of from 1 to 12 carbon atoms, more usually of from 1 to 10 carbon atoms, preferably of from 1 to 8 carbon atoms, and more preferred of from 1 to 5 carbon atoms, having from 1 to 2 alpha-chalcoxy groups, where 2 alpha-chalcoxy groups may be taken together to form a cyclic ketal of from 5 to 6 annular members and one chalcoxy group may be taken together with $\beta''$ to form an expoxide ring; Γ''' may be substituted with aliphatically saturated hydrocarbyl groups—alkyl, cycloalkyl, or carbocyclic aryl groups—of from 1 to 8 carbon atoms, more usually of from 1 to 6 carbon atoms and when other than aryl, of from 1 to 2 carbon atoms, particularly methyl.

There are two primary intermediates which find use in this invention: (1) the fragment which provides the initiator; and (2) the fragment which provides the terminator.

The fragment which provides the initiator will normally be of the formula:

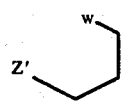

wherein:

Z' is of the formulas:

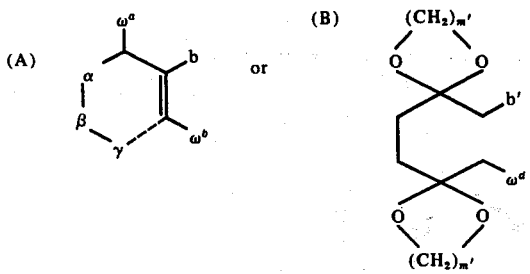

wherein all of the symbols have been defined previously except:
b' is hydrogen or alkyl of from 1 to 3 carbon atoms;
m' is an integer of from 2 to 3;
$\omega^d$ is a bond; and
w is halo of atomic number 17 to 53, triphenylphosphonium or ethinyl.

Usually, when Z' is formula A, Z' will be of the formula:

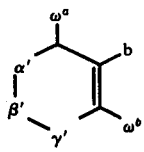

wherein all of the symbols have been defined previously.

The terminator fragment will for the most part have the following formula:

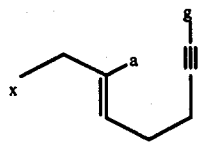

wherein a and g have been defined previously and x is formyl, carboxy or of the formula:

wherein e has been defined previously and y is hydrogen or hydroxyl.

II. Methods of Preparing Intermediates

The intermediates described in Section I are prepared by the condensation of two units which provides for the $\Delta^3$ double bond of Y. The double bond can be introduced either by condensation between a phosphonium ion and an aldehyde under Schlosser-Wittig conditions or by condensation of an aldehyde and an acetylide, with subsequent reduction of the propargyl to an ethylenic bond. Both of these procedures provide for product having a predominant amount of the trans configuration, which is the natural configuration of the steroid product. Therefore, on cyclization the desired ring fusion is obtained. The preparation of the various fragments, which contain the Z group for condensation with an aldehyde, has appeared in a number of references and will be further disclosed in the experimental section. The following publications are therefore cited to demonstrate the synthesis of a number of different Z group containing fragments.

Johnson, Accounts of Chem. Research, 1968, 1; Johnson, et al., J. Am. Chem. Soc., 90, 299 (1968); Johnson and Schaaf, Chemical Comm., 1969, 671; Abrams, et al., Bioorganic Chemistry, 1, 243 (1971); Johnson, et al., J. Am. Chem. Soc., 93, 4332 (1971); Johnson, et al., ibid, 92, 4461 (1972). U.S. Pat. Nos. 3,558,672 and 3,598,845 and German Offenlegungsschrift Nos. P22 34 018.7 and P24 18 877.0.

The Schlosser-Wittig reaction combines in an ethereal solvent approximately equimolar amounts of the ylide, particularly the triphenylphosphonium ylide, with the appropriate aldehyde. An ethereal solvent is employed, e.g. tetrahydrofuran, diethyl ether, dimethoxyethylene and combinations thereof. The temperature will normally be about $-90°$ to $-50°$ C and the concentration of reactants will generally be from about 0.05 to 1M, usually from about 0.1 to 0.5M. Carbocyclicaryl lithium, e.g. phenyl lithium is added in at least about equimolar amount and usually in excess, ranging from about 1 to 2 moles per mole of ylide-aldehyde reactant. The temperature is allowed to rise to from about $-50°$ to $-10°$ C and after a sufficient time, e.g. 5 min to 1 hour, the reaction is quenched, e.g. by addition of a lower alkanol, for example, methanol. The product may then be isolated and purified according to conventional procedures.

For the condensation of the aldehyde and acetylide, the metal acetylide, e.g. lithium acetylide, is prepared by combining the mono-substituted acetylene with a hydrocarbyl, e.g. alkyl (1-6 carbon atoms) lithium in an inert solvent, e.g. ethereal, in approximately equimolar amounts. Concentrations will generally range from about 0.05 to 1M. To the metal acetylide is added the aldehyde in approximately stoichiometric amount 0.75 to 1.25 moles aldehyde per mole of acetylide at a temperature of about $-20°$ to $20°$ C for a time sufficient for the reaction to go to completion usually 0.5 to 6 hours. The product may then be isolated according to conventional techniques.

The first reaction to be considered will be reaction I, Chart 1, which will also include the preparation of an exemplary cyclopentene Z group. The following flow chart indicates the sequence of reactions, as well as the reagents involved.

Chart 2

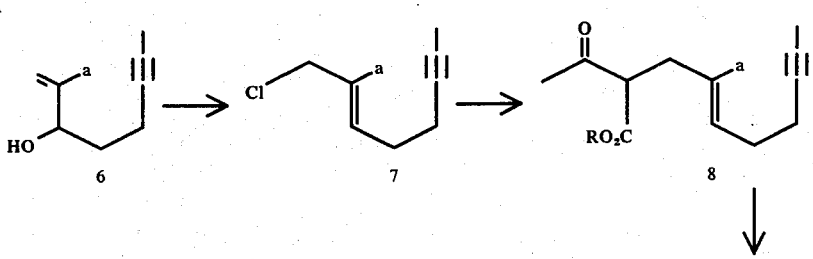

-continued
Chart 2
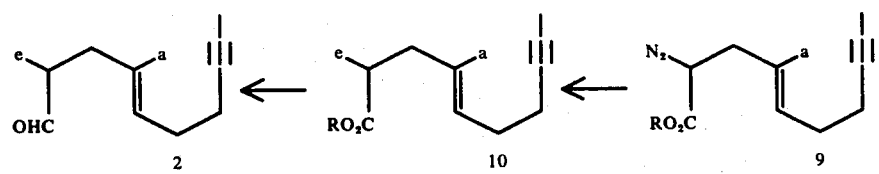
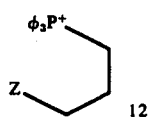
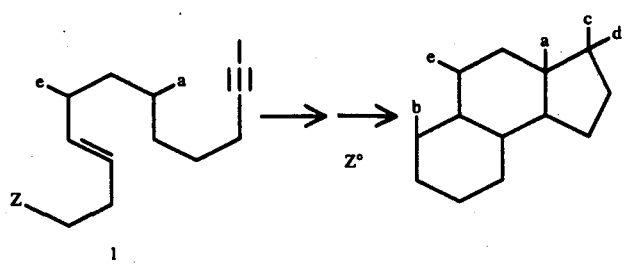
B
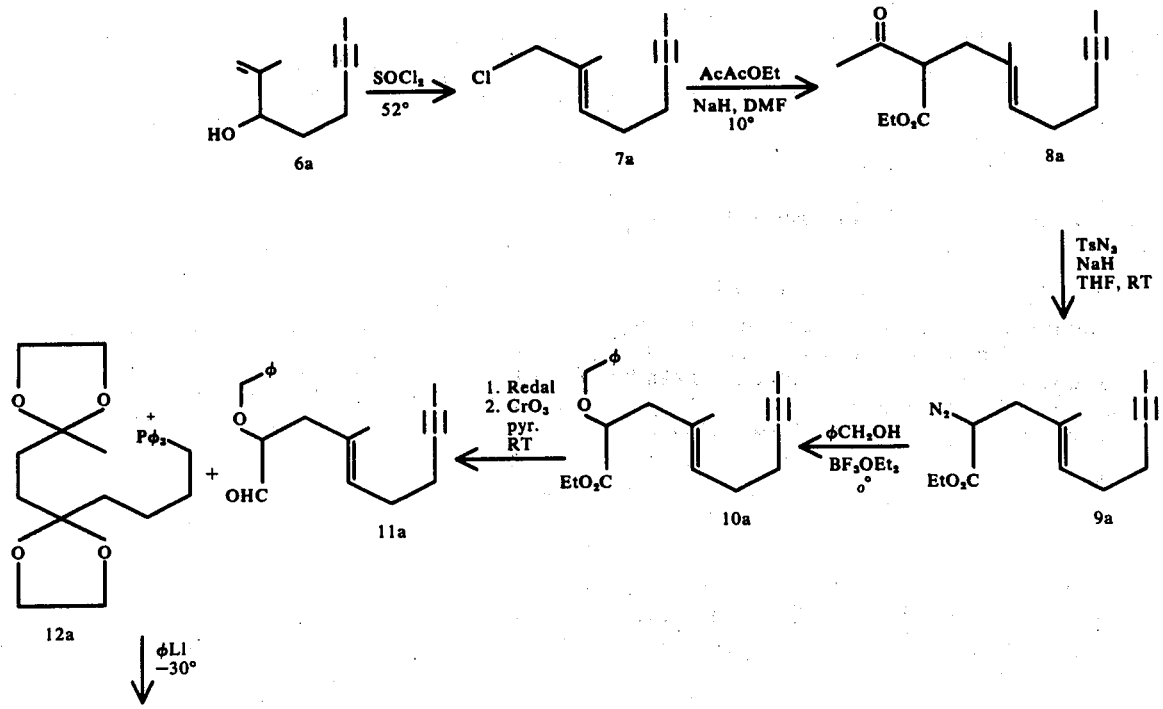

-continued
Chart 2

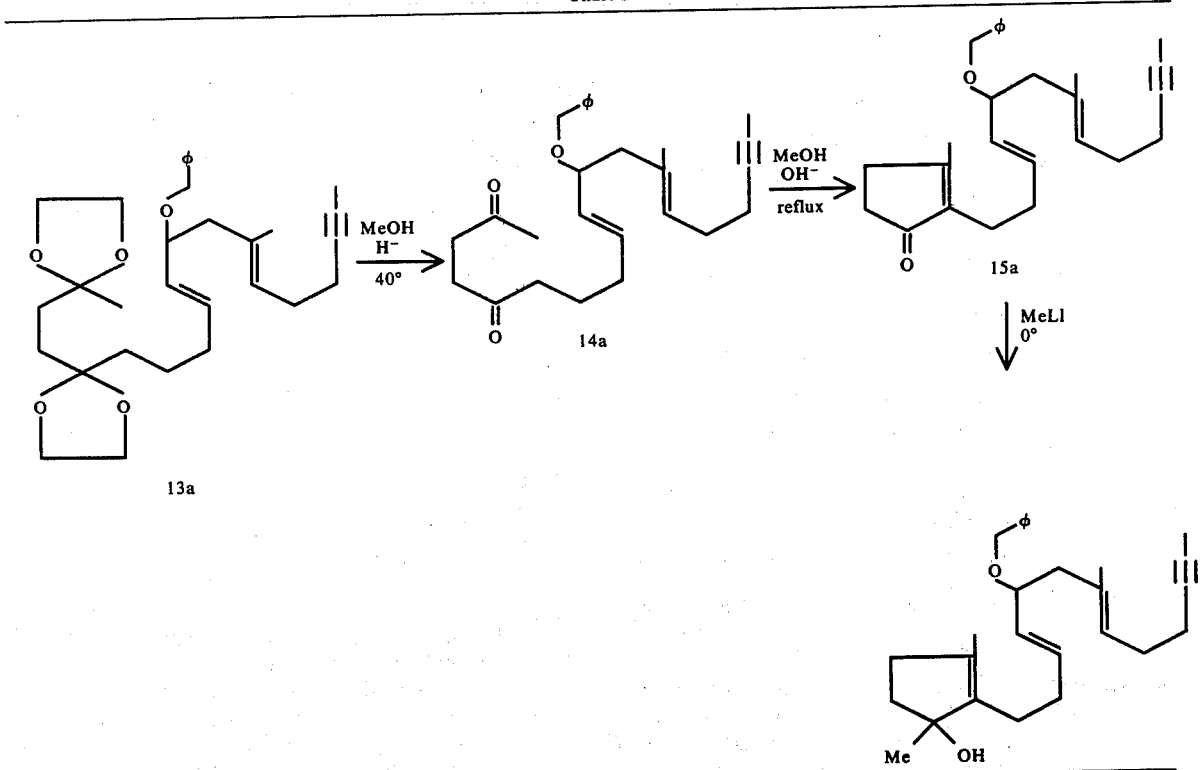
13a wherein:
Z, Z°, a, b, c, d and e have been defined previously and R is an alkyl of from 1 to 6 carbon atoms.

For the preparation of other Z groups employing the Wittig phosphonium method of condensation, see the following articles: J. A. C. S., 95, 2656 (1973); ibid, 94, 8225, 8228, 8229 (1972); J. Chem. Soc., 1131 (1957); J. Org. Chem., 36, 1137 (1971); J. A. C. S., 93, 4330 (1971); and J. Org. Chem., 27, 1615, 1620 (1962). The methods described in these articles may require some modification for producing a specific Z group, such as condensation of methyllithium with a ketone, to form a tertiary hydroxy group, reduction of the ketone to an alcohol, or the like. By preparing the appropriate haloalkyl substituted cyclohexene, the haloalkyl cyclohexene may be condensed with triphenylphosphine and by addition of phenyllithium, the phosphonium salt may be condensed with the appropriate aldehyde to provide the precursor to the polycyclic compound. The following chart indicates the reaction sequence.

Chart 3

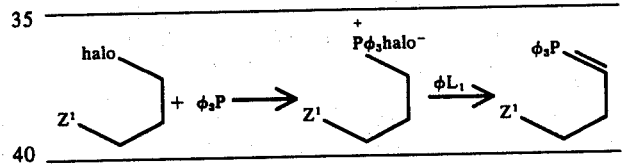

wherein Z' is the same as Z or a group which by modifications indicated previously will form Z after the condensation with the aldehyde and halo intends halogen of atomic number 17 to 53, particularly 17 to 35.

It should be noted that in place of the benzyloxy group, which after cyclization is in the 11-position, other functionalities may be present which include hydrocarbyloxy of from 1 to 10 carbon atoms, particularly 1 to 8 carbon atoms, including alkoxy and aralkoxy, hydroxy and trihydrocarbylsilyloxy of from 3 to 24 carbon atoms, particularly aliphatically saturated.

The next sequence of reactions which will be considered is the sequence involving reaction II of Chart 1. The following chart indicates the series of reactions involved in an exemplary preparation.

Chart 4

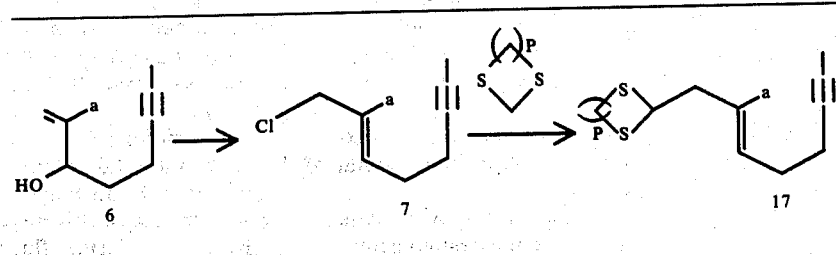

Chart 4 -continued

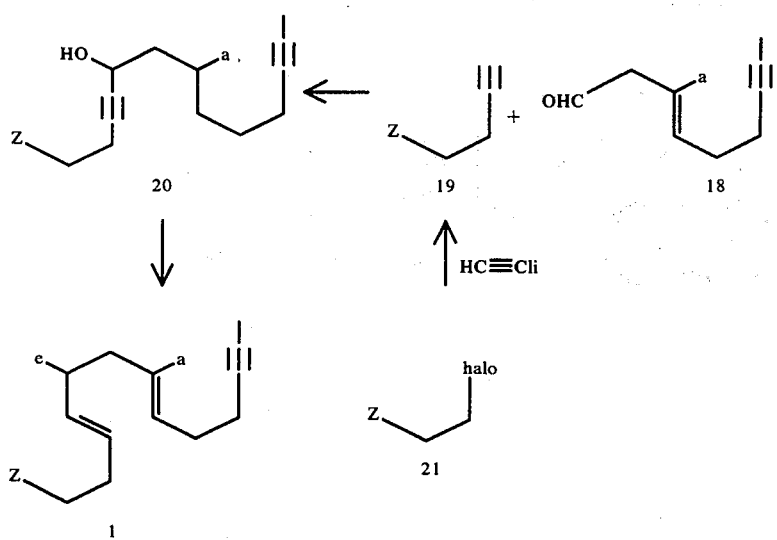

wherein Z, e and a have been defined previously, halo is halogen of atomic number 17 to 53, and p is an integer of 2 to 3.

The hydroxyl group can be modified in a variety of ways, esterified, etherified, as well as replaced by halogen, either before or subsequent to the cyclization of the diol. The hydroxyl group is introduced by virtue of the condensation of an acetylide with the aldehyde. The reduction of the acetylenic group is found to give a small amount of allene which may be separated from the acetylenic product. The reduction is found to give the desired trans configuration of the double bond, so that the product may then be used for the cyclization to the pregnane configuration.

Besides the cyclopentenol as the Z group, the other groups indicated as appropriate for Z may be employed and the reaction sequence followed, except as to the obvious differences involved with the preparation of the cyclopentenol and its yet to be described cleavage and recyclization as compared to initially employing a six-membered ring.

The significant steps in the reaction sequence are the condensation of the acetylide with the aldehyde and the reduction of the central triple bond to a trans-double bond. The acetylenic group bonded through an aliphatic chain to the initiator is combined with an alkyl metal reagent, e.g. alkyl lithium of from 2 to 6 carbon atoms, in an inert, preferably polar, solvent, e.g. ethereal at temperatures in the range of −50° to 10° C, the metal alkyl being added in approximately stoichiometric amounts or slightly less ( ≤ 10 mol %).

To the aldehyde is added the metal acetylide, e.g. lithium acetylide at moderate temperatures (−10°–25° C) and the reaction allowed to proceed to completion, usually in about 0.25 to 6 hours. Concentrations of the reactants will generally range from about 0.1 to 2M.

The product may then be isolated by conventional techniques, after mild acidification to form the alcohol from the metal alkoxide.

The central triple bond of the resulting α-hydroxydiyne is reduced to a trans-olefinic bond with a metal hydride, e.g. lithium aluminum hydride.

In accordance with the subject invention, polyenyne compounds are prepared which have the desired geometry, so that on cyclization the steroidal product has the naturally occurring configuration. During the course of the reaction, the double bonds, which are introduced, are introduced in such a manner as to provide the necessary geometry, without affecting the geometry of the substituents. In addition, the precursor having the C-11 substituent may be resolved to the desired stereoisomer, so that on cyclization, by virtue of asymmetric induction, the naturally occurring product may be obtained directly without further separation. Thus, the synthetic procedure provides routes to a cyclization precursor or intermediate which allows for great flexibility in the introduction of various substituents, both hydrocarbon and hetero at a variety of positions, particularly C-10, C-11, C-13 and C-17.

III. Cyclization

The cyclization of the polyunsaturated substituted carbocyclic ring is catalyzed by a strong acid, usually carboxylic, particularly a halocarboxylic acid having halo at the α-position, and more particularly, a perhalocarboxylic acid, usually chloro or fluoro, preferably fluoro and of from 2 to 4 carbon atoms, particularly 2 carbon atoms. For the most part, carboxylic acids are employed having a pK at 25° C of less than about 4.

The solvent is a protic solvent, particularly an organic chalcoxy solvent, e.g. hydroxylic solvent of from 2 to 4 carbon atoms, preferably 2 carbon atoms, preferably a halochalcoxy solvent, e.g. a haloalkanol, wherein the halogen is of atomic number 9 to 17, particularly fluoro and chloro, and more particularly fluoro, and having at least one halogen atom per carbon atom, preferably at least 1.5 halogen atoms per carbon atom—a fraction being taken to the next higher number—and particularly preferred trifluoroethanol, wherein halogen is on other than the carbon atom bonded to the hydroxyl.

Small amounts (<25 vol. %., usually <15 vol. %, based on the total volume of the reaction mixture) of other inert solvents may be employed, which are miscible with the major solvent. Inert halohydrocarbons, e.g. methylene dichloride, fluorochloromethane, dichloroethane, etc. may be added of from 1 to 3 carbon atoms and 1 to 8 halogen atoms, particularly fluorine and chlorine. Water may also be present, not only from the dehydration of the substrate but also adventitiously present in small amounts where the intermediate product has not been dried.

The reaction will normally be carried out in an inert atmosphere at temperatures in the range of about −10° to 40° C, usually −5° to 30° C, and preferably from about −5° to 25° C, and more preferably 0° to 25° C. The time for the reaction will vary widely, but will be at least about one hour and may be 2 weeks or more, usually being at least about 1.5 hour, and generally not more than 96 hours, but at least the minimum time to provide the desired yield. While the product appears to form relatively rapidly, based on spectral data, substantially enhanced yields are obtained by extending the reaction time. It is thus found that it is preferable to increase the time with increasing electronegativity of the C-11 substituent. Ambient pressures are normally satisfactory.

The concentration of the reactant based on solvent (not including the acid catalyst) will generally range from about 0.01M to about 0.1M, more usually from about 0.005M to 0.05M. While the concentration is not critical, relatively dilute solutions will be employed to minimize the opportunity for polymerization.

The mole ratio of the acid to the cyclization substrate may also be varied quite widely, above a minimum related to the C-11 subsituent, without substantial effect upon the course of the reaction. Normally, at least about 5 moles of the carboxylic acid will be employed per mole of substrate, more usually at least 10, and generally not more than about 750 moles, more usually not more than about 500 moles of carboxylic acid, per mole of cyclization substrate.

The molar concentration of the acid catalyst will generally be from about 0.5 to 15M, more usually about 1 to 10M, and preferably about 2 to 5M. Increasing molarity is desirable to enhance the yield of the desired product.

The order of addition is not critical. The acid may be added to the substrate in solution or the substrate may be added to the acid in solution. Normally, the acid and substrate will not be combined except in the presence of solvent.

Depending on the solvent system and acid reagent, various moieties will serve as the nucleophile. In the presence of water, both the water and acid may compete for the carbocation. Various other molecules may be present which are capable of forming a stable covalent bond with the carbocation. With the vinyl carbocation being captured by water, oxo will be formed directly. Otherwise, vinyl esters and ethers may be isolated. These may then be hydrolyzed to the C-20 oxo group.

The workup may follow conventional techniques, whereby the acid is neutralized with a mild base and the product extracted by any convenient solvent. The product may then be purified by any convenient preparative means such as chromatography, solvent-solvent extraction, etc.

IV. Tetracyclic Products

The cyclic products, which are formed in accordance with the subject invention, will have from about 19 to 45 carbon atoms, usually from about 19 to 36 carbon atoms, and more usually from about 20 to 36 carbon atoms, generally having from about 20 to 30 carbon atoms when X is propargyl and from about 25 to 35 carbon atoms, when X is phenylethinyl.

For the most part, the tetracyclic compounds formed by the subject cyclization will have the following formula:

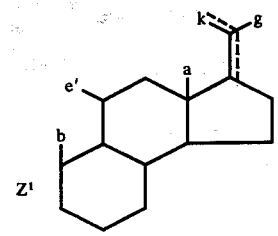

wherein:

$a$, $b$ and $g$ have been defined previously, $e'$ is $e$ plus carboxyester of from 1 to 12 carbon atoms, usually 1 to 6 carbon atoms, e.g. formate, acetate, pivalate, benzoate, etc. and $Z^1$ is a di- or trivalent organic radical which forms a ring of from 5 to 6 annular members with the carbon atoms to which $Z^1$ is attached and has from 0 to 2 chalcoxy groups or 0 or 1 oxo group and has from 1 to 2 sites of ethylenic unsaturation, there being 1 endo-double bond, which may be subsequently hydrogenated. When $Z^1$ is trivalent, there is a double bond to a bridgehead carbon atom. $Z^1$ is normally of from about 3 to 9 carbon atoms, usually of from 3 to 7 carbon atoms, and preferably of from about 4 to 7 carbon atoms and 0 to 2 chalcogen atoms. There is one double bond between the carbon atoms and K signified by the broken line. When the double bond is between the carbon atoms, $k$ is a carboxy ester of from 2 to 4 carbon atoms and 1 to 6 halogen atoms of atomic number 9 to 17, e.g. trifluoroacetoxy, while when the double bond is between the carbon atom and $k$, $k$ is oxygen.

Illustrative $Z^1$ groups include:
but-1-en-1,4-ylene;
3-methylprop-1-yl-3-ylidene;
2-(2'-thiolethylenethio)but-1-en-1,4-ylene;
3-isopropylidenebut-1-yl-4-ylidene;
3-ethylprop-1-yl-3-ylidene; and
3-oxobut-1-yl-4-ylidene.

When the cyclization is carried out with a cyclopentenol compound, the resulting product will for the most part have the following formula:

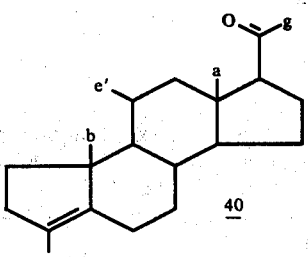

wherein:

$a$, $b$, $e'$ and $g$ have been defined previously, and $j$ is hydrogen or alkyl of from 1 to 4 carbon atoms, usually of from 1 to 2 carbon atoms, and more usually methyl.

Upon oxidation of the endocyclic double bond, for example, ozonization, the ring is opened to a diketone. In addition, if a substituent at C-11 has aliphatic unsaturation, that double bond will also be cleaved to provide an aldehyde or carboxylic acid depending upon the method of workup. The product of oxidation will have the following formula:

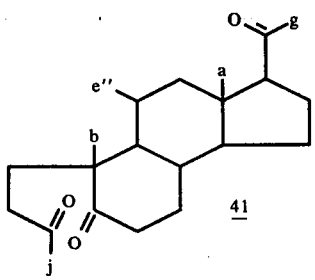

wherein:

a, b, g and j have been defined previously, and e'' is a chalcoxy group as defined previously.

When j is other than hydrogen upon base catalyzed condensation, the A ring is reformed to form a product of the following formula:

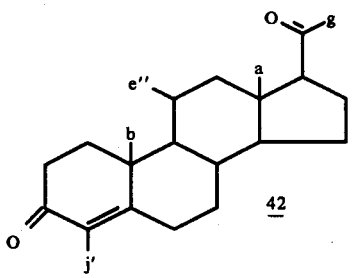

wherein:

a, b, e'' and g have been defined previously, and j' is hydrogen or alkyl of from 1 to 3 carbon atoms, usually of 1 carbon atom and preferably hydrogen.

Where the initiator is a cyclohexenyl group, the resulting product will for the most part have the following formula:

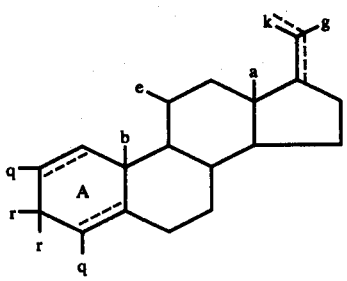

wherein:

a, b, e, k and g have been defined previously;

the meaning of the broken line between C-17 and C-21 has been defined previously;

one of the broken lines in the A ring is a double bond, particularly $\Delta^1$, The q bonded to the ethylenic carbon atom is H or β or γ hydrochalcoxy-(OH or SH)-alkylenechalcoxy (alkylene of 2 to 3 carbon atoms), the other q is hydrogen; and the two r's are hydrogen or may be taken together to form alkylidene of from 1 to 4 carbon atoms, a cyclic oxy or thio ketal or oxo.

Depending on the other Z groups involved, various transformations of the functionalities present in the Z group will be appropriate. Ketones can be reduced to alcohols, double bonds introduced into the ring, exocyclic double bonds cleaved by ozonation and the like.

The cyclization provides the substituted steroids at the C-11 with the alpha-configuration. Since this configuration has shown physiological activity in steroid derivatives, the fact that it is obtained directly without the presence of significant amounts of the beta-configuration allows for direct synthesis to the alpha-configuration without the need to separate mixtures of the two isomers. In addition, since the intermediates can be resolved at an early stage, the alpha-C-11 isomer can be provided optically active.

EXPERIMENTAL

The following examples are offered by way of illustration and not by way of limitation.

(All temperatures not otherwise indicated are in Centigrade. All percents not otherwise indicated are by weight. The phrase "worked up in the usual manner" means the organic layer is washed with brine, dried over anhydrous magnesium sulfate, filtered, and the solvent removed in vacuo. Where a number is indicated with a compound, it relates to the number in an earlier chart or an independently designated number).

CHART 2 COMPOUNDS

Example 1 a. 3-Carboethoxy-6-chlorohept-5-en-2-one (cis/trans)

To a solution of 46g sodium (2g atom) in 500ml ethanol at reflux, in a 2-liter flask equipped with mechanical stirrer, and addition funnel, was added 325 g ethyl acetoacetate (2.5 mole) over 30 minutes. The resulting solution of enolate was refluxed for 15 minutes, and then 250g (2.0 mole) 1,3-dichlorobut-2-ene was added dropwise at such a rate as to maintain reflux with gentle heating towards the end of the addition. After addition, refluxing and stirring were maintained for 4 hours, the condenser converted for distillation, and ethanol removed as 500ml distillate. The residual product was cooled, water and 1.2N hydrochloric acid were added and the organic layer separated. The aqueous portion was extracted with ether, the organic layers combined, washed with water and brine, filtered through sodium sulfate and evaporated in vacuo to give 485g dark yellow oil (96%, based on dichlorobutene). Vpc showed 73% of trans plus cis product, together with other volatiles.

b. Methyl 4-hexynoate.

Crude 3-carboethoxy-6-chlorohept-5-en-2-one from part (a) above, (242g) was added dropwise (at such a rate as to maintain reflux) to 264g (4 mole) 85% potassium hydroxide dissolved in 250ml 95% ethanol in a 2-liter 3-necked flask equipped with mechanical stirrer, reflux condenser and addition funnel. After the addition the condenser was converted for distillation, 150ml ethylene glycol and 50ml 2-ethoxyethanol were added, and ethanol/water distilled off until the pot-temperature had reached 130°-135°. Stirring and heating under reflux were continued for 5 hours at 130°-135°, the reaction mixture cooled to about 80°, 1 liter brine added, the mixture stirred for 2-3 hours at room temperature and then poured into a separatory funnel. After washing with ether (3 × 150ml), the aqueous solution was then acidified with cold concentrated hydrochloric acid to pH 6.5, extracted with chloroform, acidified to pH 1.0, and again extracted with chloroform. The pH 1.0 extracts were washed with 200ml brine, filtered through sodium sulfate and evaporated in vacuo to give 67.1g (60% based on dichlorobutene) pale brown crystalline solid (after removal of acetic acid by azeotroping with 1,4-dioxan and vacuum drying). A small sample of the acid was purified by crystallization from benzene: pentane and vacuum sublimation to give 4-hexynoic acid, colorless needles, m.p. 99°–100°.

The crude acid was dissolved in 150ml dry methylene dichloride and 48g methanol, and refluxed for 20 hours with 0.50g p-toluenesulfonic acid monohydrate. The reaction mixture was cooled, diluted with saturated sodium bicarbonate solution, separated and the aqueous layer extracted with ether. The combined organic extracts were washed with saturated sodium bicarbonate solution and the product isolated to give 58g orange oil. Distillation in vacuo through a small Vigreux column gave 51.0g methyl 4-hexynoate as colorless oil, b.p. 77°–78°/21mm.

c. 4-Hexynal.

4-Methyl hexynoate (25.0g, 0.20 mole) was dissolved in 100ml dry tetrahydrofuran in a 500ml flask equipped with mechanical stirrer and addition funnel with provision for "Dry-Ice"/acetone cooling. To the stirred solution at −70° under dry $N_2$ was added over 1 hour, 70ml of a 3.54M solution of sodium bis(2-methoxyethoxy)aluminum hydride (Redal) in benzene diluted to 140ml (total volume) with dry tetrahydrofuran from the cooled addition funnel. The product was then stirred for 5 hours at −70° and then 14.2ml (11g, 0.25 mole) acetaldehyde, was added slowly by syringe. After 10 minutes at −70° the reaction mixture was poured into a mixture of 100ml concentrated hydrochloric acid and 500ml saturated brine. The mixture was ether extracted and the extracts washed with 50ml saturated sodium bicarbonate solution and with 50ml brine, then filtered through $Na_2SO_4$ and evaporated in vacuo at RT. The crude 4-hexynal was used directly for the next step after drying over "4A"-molecular sieves to remove ethanol.

d. 2-Methyloct-1-en-6-yn-3-ol, 6a

Magnesium (14.4g, 0.6g atom) was dried in a 250ml flask fitted with reflux condenser, mechanical stirrer and addition funnel. After initiation of reaction under dry $N_2$ with about 1 ml ethylene dibromide in 70ml tetrahydrofuran, 36.0g (0.30 mole) 2-bromopropene was added dropwise at such a rate as to maintain reflux without external heating. The Grignard solution was then stirred until it cooled to room temperature (30 minutes-1hour). It was then cooled further to −15° in ice-salt, and the total crude 4-hexynal from part (c) above was added dropwise over 15 minutes. The reaction mixture was stirred for 2 hours at room temperature, saturated ammonium chloride solution was added and the product was extracted with ether. There was obtained 23.50g of 2-methyloct-1-en-6-yn-3-ol (85%, based on 4-methyl hexynoate) as a pale yellow oil.

Apart from small samples for characterization, the alcohol was rather unstable to distillation or chromatography, and was used crude in the next step for best overall yields.

EXAMPLE 2

1-Chloro-2-methyloct-2-en-6-yne, 7a

A mixture of 3-hydroxyoct-1-en-6-yne 6 (0.73g, 5.26 mmoles, dry to $MgSO_4$) in hexane (dry to $Al_2O_3$, 15ml) and thionylchloride (1.36ml, fresh-dried from P(OEt)$_3$) was heated to 52° under $N_2$ for 2.2 hour. The excess thionyl chloride was removed under reduced pressure (rotary), leaving a dark residue. The residue was dissolved in hexane (50ml) and the organic phase washed with water (twice, 15ml each), bicarbonate (twice, 15ml each) and brine (once, 25ml). Evaporation of the dried ($MgSO_4$) organic phase yielded a brown liquid, which was chromatographed on Florisil (40g, Fisher, 100–200 mesh, hexane elution). The combined chloride fractions were distilled (110° at 1.0mm, Kugelrohr) affording the primary chloride 7 (0.51g, 62%) contaminated with isomeric secondary chloride.

EXAMPLE 3

1-Chloro-2-methyl-2trans-octen-6-yne, 7a

A mixture consisting of 85% of 1-chloro-2-methyl-2trans-octen-6-yne and 15% of 3-chloro-2-methyl-1-octen-6-yne (3.2g) was fractionated in a small spinning band apparatus (Nester Faust, microstill) at 9mm. When the pot residue was shown to contain the desired less volatile trans isomer in greater than 98% purity, the distillation was interrupted, and the residue was freed from some black junk by bulb-to-bulb distillation at 120°/9mm.

EXAMPLE 4

Ethyl 2-acetyl-4-methyldec-4-en-8-ynoate, 8

Sodioethylacetoacetate (ethyl acetoacetate, 15.6272g, 0.12 moles; NaH dis., 2.2137≈0.052 moles) in DMF (CaH$_2$ dried, 25ml) at ~10°, was treated with allylic chloride 7a (3.65g, 23.4 mmoles). Following 10 minutes at 10°, the solution was stirred at RT for 20 hours, then poured into hexane. The organic layer was washed with water, bicarbonate, and brine; then dried ($MgSO_4$). Removal of the volatiles, in vacuo, and chromatographic purification of the product (Florisil, 40g, elution with 20% ether in hexane) followed by distillation (12μ at 95°), afforded ethyl ester 8a (4.55g, 78%).

EXAMPLE 5

Ethyl 2-Benzyloxy-4-methyl-dec-4-en-8-ynoate, 10a

A. Ethyl β-ketoester 8a (2.48g, 9.88 mmoles) in THF (2ml) was added to a suspension of NaH (dispersion, 0.79g ~ 18.9 mmoles) in THF (6ml), over a 20 minute period. After 1 hour of stirring at RT, p-toluenesulfonylazide (3.58g, 18.2 mmoles) was added with cooling. The yellow suspension was stirred 1 hour, filtered, and hexane added to the mother liquor producing a heavy precipitate. The precipitate was removed by filtration, leaving a clear yellow green mother liquor. Removal of the volatile components of the solution (rotary evaporator) yielded a mobile yellow residue that was used in the next reaction without further purification.

B. Crude diazoester 9 (from previous step ~3ml) was dissolved in benzylalcohol (10ml) and ether (10ml) and BF$_3$OEt$_2$ (5 drops) added at 0°. After 10 minutes, the alcoholic solution was poured into ether and bicarbonate. The ether layer was separated, washed with brine, and dried (MgSO$_4$). Volatiles were removed and the residue was chromatographed on silica gel (180g, elution with 10% ether in hexane), then rechromatographed (Florisil, 150g, 4% ether in hexane). This afforded a quantity of ester still as a mixture with azide (~1.00g of ester) and pure ester. The latter was distilled (Kugelrohr, 90° C at 12$\mu$) affording 2.21g (38.4%) of pure ester.

EXAMPLE 6

2-Benzyloxy-4-methyl-dec-4-en-8-yn-1-al, 11a

A. To benzyloxy ester 10a (2.1886g, 6.94 mmoles) in THF (8ml), was added Redal (3ml 10.5 mmoles) at water bath temperature. After 1½ hour, water and ether were cautiously added. The resulting two phase system was made acidic (10% HCl) and the organic layer separated, washed with bicarbonate and brine, then dried (MgSO$_4$). The volatiles were removed and the residue chromatographed (Florisil, 40g, elution with 17% ether in hexane) and distilled (75° C at 10$\mu$) affording alcohol ether intermediate (1.73g).

B. Chromium trioxide (dry, 0.96g, 9.6 mmoles) was added to methylenechloride (20ml, dry) and pyridine (1.55ml, 1.52g, 19.5 mmoles) under N$_2$ at RT. The red solution was stirred for ½ hour. The alcohol prepared above (0.38g, 1.4 mmoles) in methylene chloride (2ml) was added. After 1⅓ hour, the reaction solution was poured into bicarbonate and ether added (70ml). The organic layer was separated washed with additional bicarbonate, 10% HCl, bicarbonate, and brine. The dried (MgSO$_4$) organic solution (brown-clear) was filtered through Florisil (~2g) and concentrated, in vacuo, yielding a viscous oil, aldehyde 11a (0.35g, 94%).

EXAMPLE 7

Benzyloxybisketal, 13a

Phosphonium salt 12a (0.97g, 1.55 mmoles) in THF (17ml) was treated with phenyllithium (1 eq in 5.3ml ether) at 0°. The temperature was gradually lowered to −78° and aldehyde 11a (0.35g, 1.3 mmoles) was added in ether (5ml). After 10 minutes at −78°, the mixture was warmed to −30°, phenyllithium (1 eq in 5.3ml ether) and ether (THF to ether ratio is 1 to 1) were added. After 10 additional minutes of reaction time, methanol (0.12ml) was added, the bath was removed, and the solution left overnight. Ether was added and the mixture was washed with water and brine, dried (MgSO$_4$) and concentrated in vacuo. Repeated chromatographic separation of the products (over prep TLC, 1:1 hexane-EtOAc; silica gel = column-elution with 10% ether in hexane; prep TLC, 2 to 1 hexane-EtOAc) afforded benyzloxybisketal 13a (0.38g, 49%).

EXAMPLE 8

Benzyloxydiketone, 14a

Bisketal 13a (0.38g, 0.77 mmoles) was added to methanol (13.5ml) and 0.1 N HCl (3.5ml). The cloudy solution was heated at 40° overnight (N$_2$). The cooled solution was concentrated, poured into bicarbonate and ether added. The organic layer was separated, washed with brine, then dried (MgSO$_4$). Removal of the volatiles yielded a yellow oil diketone 14a (0.28g, 88%).

EXAMPLE 9

Benzyloxycyclopentenone, 15a

Benzyloxydione 14a (0.28g, 0.67 mmoles) was dissolved in methanol (15ml) and 5% NaOH aq (8ml) added (N$_2$). The solution was heated under reflux for 2.76 hour, cooled, and concentrated under reduced pressure. Ether was added and the organic phase separated, washed with brine, then dried (MgSO$_4$). Removal of the volatiles and purification (prep. TLC, 1:1 hexane to EtOAc) afforded pentenone 15a (0.24g, 91%).

EXAMPLE 10

Benzyloxyallylic alcohol, 16a

Cyclopentenone 15a (0.07g, 0.19 mmoles) in ether (7 ml) at 0° (N$_2$) was treated with methyllithium (excess, using phenanthroline indicator). The reaction was quenched in 10 minutes with water (3ml) and the organic phase separated (dried over MgSO$_4$). Removal of the voltiles afforded crude alcohol 16a (0.08 g, >100%).

CHART 4 COMPOUNDS

EXAMPLE 11

3-Methyl-1-(propylenedithio)-3-trans-nonen-7-yne, 17a

A stirred solution of 1,3-dithiane (3.0g, 25mmoles) in anhydrous tetrahydrofuran (25ml distilled from LAH) was treated under argon with n-butyllithium-hexane (Ventron, 2.25m, 11.3ml, 25.5 mmoles) at −25°. After 1.5 hours at −25° to −20°, the solution was cooled to −70° and the chloride 7a (3.85g, 25 mmoles) in tetrahydrofuran (5 ml) was added. The yellow to orange colored mixture was warmed up to −40°, put in the freezer (−20°) overnight, then allowed to come to room temperature (1 hour). After quenching the reaction with water, the mixture was partitioned between ether and brine. The organic layer was washed with two more portions of brine, dried over potassium carbonate and evaporated to give 6g of crude compound. Chromatography on 180g of silica gel with hexane-ether 19:1 afforded 5.13g (85%) of the thioacetal 17a as a thick, almost colorless oil, homogeneous by tlc and ~98% pure by vpc.

EXAMPLE 12

3-Methyl-3-trans-nonen-7-yn-1-al, 18a

Methyl iodide (3.0ml, 50 mmoles) was added dropwise to a vigorously stirred and argon-flushed mixture of the thioacetial 17a (1.20g, 5 mmoles), calcium carbonate powder (2.0g, 20 mmoles), and acetonitrile - water 4:1 (25ml). The mixture was stirred under nitrogen at room temperature for 14 hours diluted with ether and washed three times with ice-water. The aqueous layer was dried over magnesium sulfate and evaporated at room temperature/9mm; 742mg, (99%) of the crude aldehyde 18a were obtained.

EXAMPLE 13

2,5-Bis(ethylenedioxy)-9-decyne, 19a

A. In a 1-liter 3-necked flask equipped with nitrogen inlet, mechanical stirrer and a Dean-Stark trap with condenser were placed 500ml of benzene, 180ml of ethylene glycol (200g, 3.2 moles), 3.0g of para-toluenesulfonic acid monohydrate and about 100mg of hydroquinone. The mixture was stirred and refluxed for 6 hours to remove any water. Then 111g of 2-methyl-5-(3'-bromopropyl)furan (0.51 mole) was added, the flask shielded from light and stirring and reflux continued. After 43 hours, the mixture was allowed to cool and poured into a separatory funnel, and the brown glycol layer allowed to separate. The benzene layer was washed with saturated bicarbonate (2 × 100ml), then with brine (2 ×]50ml), filtered through anhydrous sodium sulfate and the solvent removed under reduced pressure to give 158g (165g theoretical) of pale yellow-brown liquid. The crude product (69g) was applied to a column of 1kg of 100–200 mesh Florisil (activated magnesium silicate). Unreacted bromofuran (9.5g) was eluted with hexane. The desired 1-bromoocta-4,7-dione bis(ethylene ketal) 21a (51g, 71% conversion, 88% yield corrected for recovered starting material) was eluted with 15% ether in hexane.

B. A well-stirred slurry of lithium acetylideethylenediamine complex (4.56g, 49.6 mmoles) in anhydrous dimethyl sulfoxide (20ml; distilled from calcium hydride) was slightly cooled in ice-water. The bisketal bromide 21a (7.67g, 24.8 mmoles) prepared above in dimethyl sulfoxide (5 ml) was added over a period of 10 minutes. The brown-red solution was stirred at room temperature for 50 minutes. After cautious hydrolysation by dropwise addition of ice-water, the mixture was partitioned between water and ether. The ether layer was washed twice with brine, dried over anhydrous magnesium sulfate and evaporated to give 5.9g of crude compound. Column chromatography on 200g of silica gel afforded 4.40g of pure bisketal acetylene 19 as a clear liquid. Fractions (1.09g) which were contaminated with some less polar impurities were rechromatographed on 130g of silica gel to give another 0.74g of pure compound. Total yield of product 19a: 5.4g (81.5%).

EXAMPLE 14

2,5-Bis(ethylenedioxy)-11-hydroxy-13-methyl-13trans-nonadecen-9,17-diyne, 20a

A stirred solution of the bisketal acetylene 19a (1.90g, 7.5 mmoles) in anhydrous 1,2-dimethoxyethane (21ml distilled from LAH) was cooled to −20° under nitrogen atmosphere. n-Butyllithium-hexane (2.4m, 3.1ml, 7.4 mmoles) was added dropwise. After 30 minutes, a freshly prepared batch of the aldehyde 18a (1.00g, 6.65 mmoles) in 6ml of 1,2-dimethoxyethane was added, and the mixture was allowed to come to 0° (1 hour). After another 30 minutes at room temperature, the reaction was quenched with cold, aqueous ammonium chloride and extracted with ether. The organic layer was washed with brine, dried over potassium carbonate and evaporated. The residue (2.85g) was chromatographed on 70g of aluminum oxide, neutral, activity III. Hexane-ether 4:1 eluted some apolar impurities and the excess of the bisketal acetylene 19 (371mg). Hexane - ether 1:1 and ether afforded the proparglyic alcohol 20a (2.33g, 87%) as a colorless, thick oil, suitably pure for the next step.

EXAMPLE 15

2,5-Bis-(ethylenedioxy)-11-hydroxy-13-methyl-9trans, 13trans-nonadien-17-yne, 13b To a stirred suspension of lithium aluminum hydride (428mg, 11.3 mmoles) in anhydrous tetrahydrofuran (46ml distilled from LAH) was added a solution of the propargylic alcohol 20a (2.33 g, 5.67 mmoles) in 23ml of tetrahydrofuran at room temperature. After being refluxed under nitrogen for 4 hours the mixture was cooled to −10°, treated slowly with cold methanol - ether 1:1 (5ml) and saturated aqueous ammonium chloride (15ml), then extracted with ether. The organic layer was washed with aqueous ammonium chloride and brine, dried over magnesium sulfate and evaporated. As judged by vpc, the ratio of the allylic alcohol 13b to the allene isomer was 94:6. Separation could easily be achieved by chromatography on 90g of aluminum oxide, neutral, activity III. Hexane - ether 4:1 afforded allene containing fractions (113mg) which were purified further. The allylic alcohol 13b (2.076g, 90%) was then eluted as a colorless, thick oil with hexane - ether 1:1 and 1:4. This batch was suitably pure for the next step.

EXAMPLE 16

3-methyl-2-(5'-hydroxy-7'-methyl-3'-trans, 7'-transtridec-dien-11'-ynyl-1')2-cyclopentenone-1, 15b A solution of the allylic alcohol 13b (1.03g, 2.5 mmoles) in pyridine-acetic anhydride (4:1, 5ml) was allowed to stand at room temperature overnight. The excess of the acetic anhydride was destroyed by the addition of 0.5ml of 85% lactic acid reagent. After 30 minutes the mixture was transferred into cold aqueous sodium bicarbonate and extracted with ether. The ether layer was washed twice with bicarbonate, three times with brine, three times with saturated aqueous cupric sulfate and twice with brine. Drying over magnesium sulfate and removal of the solvent gave 1.14g (quantitative) of the allylic acetate, homogeneous by tlc (hexane - ethyl acetate 1:1, 2×:0.56: compound 13b in the same system; 0.34).

This compound was dissolved in acetone (20ml) containing p-toluenesulfonic acid (50mg) and left at room temperature for 20 hours. A little sodium bicarbonate solution was added, and the mixture was concentrated at reduced pressure. Normal workup with ether afforded 894mg of the crude bisketone 14b which, however, was contaminated by traces of bisketal. Retreatment under the above conditions for 3.5 hours gave 863mg (96%) of now bisketal-free 14b.

A solution of the crude bisketone 14b in methanol (25ml) and 5% aqueous sodium hydroxide (15ml) was purged with argon, then kept at 70°–75° under nitrogen for 5 hours. The cold mixture was partitioned between aqueous ammonium chloride and ether. The ether layer was worked up in the usual way. The residue (725mg) was chromatographed on 90g of silica gel with hexane - ethyl acetate 6:4 (500ml) followed by hexane - ethyl acetate 1:1 to afford 562mg (75% from the allylic alcohol 13b) of the cyclopentenone 15b. The thick, slightly yellow oil was homogeneous by tlc, and ~98% pure by vpc (3% XE 60, 195°; 3% OV 17, 210°).

EXAMPLE 17

Ethylenedithioketal 3-methyl-4-(2'-bromoethyl)cyclohex-2-enone, 21b (this series of compounds has Z as the ethylenedithioketal of 3-methyl cyclohex-2-en-1-on-4yl).

A solution of 3.28g. (14.2 mmole) of the ethylenedithioketal of 3-methyl-4-hydroxymethylcyclohex-2enone and p-tosyl chloride (3.8g, 20 mmoles) in pyridine (8ml) was maintained at 0° for 23 hours and then 2ml of 85% lactic acid added. The product was then worked up in the usual manner.

A solution of the above product (4.68g) in DMSO (30 ml) containing 5.0g sodium cyanide was stirred at room temperature for 22 hours, diluted with ether, and the solution extracted with aqueous sodium bicarbonate followed by brine and then dried and evaporated to afford 3.73g of an oil. The oil was dissolved in 80ml of 50% aqueous methanol containing 4g KOH and refluxed for 24 hours. Volatiles were removed in vacuo and the residue extracted with ether. After acidification of the aqueous phase with 10% HCl, the aqueous phase was extracted with ether, the ethereal solutions dried and concentrated to leave 2.3g of a residue. The residue was dissolved in 30ml THF, 0.4g (12.4 mmoles) of LAH added and the mixture allowed to stand at room temperature for 16 hours, cooled to 0°, treated cautiously with ethanol, followed by aq. $NH_4Cl$, followed by extraction with ether. The ethereal solution was worked up in the usual manner. The crude alcoholic product, (1.32g) was dissolved in 300ml of pyridine containing 1.4g (7.3 mmoles) of p-TosCl and allowed to stand at 0° for 45 hours, the solution diluted with ether, followed by extraction with ether, washing with aqueous sodium bicarbonate, brine, aqueous cupric sulfate and brine, then dried and volatiles removed by evaporation.

The crude product (1.44g, 3.8 mmoles) was dissolved in 7 ml HMPA containing 4.0g (39 mmole) of sodium bromide and stirred at room temperature for 15 hours. The mixture was then poured into brine and the aqueous solution extracted with ether. After washing the ether solution with brine, it was dried, evaporated, and the residue chromatographed on alumina (Wolem activity III, 20g). Elution with ether/hexane (1/99) gave the desired bromide 21b as a colorless oil (700mg).

EXAMPLE 18

Ethylenedithioketal of 3-methyl-4-(butyn-3'-yl-1')-cyclohex-2-enone, 19b

To a suspension of sodium acetylide (prepared from 2.5g, 110 mmoles of sodium) in 100ml of liquid ammonia was added 0.7g (2.4 mmoles) of the bromide 21b in 20ml of THF. The mixture was agitated for 9 hours are reflux and the ammonia then allowed to evaporate. The residue was dissolved in ether, treated with aqueous sodium chloride, followed by brine, and the ethereal solution then dried and evaporated. The residue was chromatographed on alumina (Wolem activity III, 20g), eluted with ether/hexane (1/99) to yield 0.43g (76%) of the acetylene 19b.

EXAMPLE 19

1-(2'-methyl-4',4'-ethylenedithiocyclohex-2'-en-1'-yl)-5-hydroxytridec-7-en-3,11-diyne, 20b To 0.43 g (1.8 mmoles) of the acetylene 19b in 7ml dimethoxyethane (DME) was added 3.2ml of a 0.56M solution of methyllithium followed by the addition of 0.26g (1.72 mmoles) of the aldehyde 18a in 3ml DME at 0°. After 2 hours at room temperature, the solution was treated with aqueous ammonium chloride and the product isolated by ether extraction, followed by chromatography on alumina (Wolem activity III, 20g). Upon elution with ether/hexane (1/1) the propargylic alcohol 20b was obtained (0.50g, 76%).

The proparglyic alcohol 20b in accordance with the procedure of Example 15 is to provide the 3,7-diene product. The resulting product could then be used directly for cyclization.

CYCLIZATIONS

EXAMPLE 20

Preparative Cyclization Employing 2,2,2-trifluoroethanol (TFE)

A solution of 39mg of the benzyl ether 15 in anhydrous ether (5ml) was treated dropwise with methyllithium - ether (0.4 mmoles) at 0° under $N_2$. After 15 minutes the reaction was quenched with ice-cold wet ether (~3ml) followed by a spatule of anh. $K_2CO_3$. The cold suspension was filtered and the flask rinsed repeatedly with dry ether. The combined organic portions were evaporated at 0°/9mm, then 0°/0.5mm.

The tertiary alcohol 16b was dissolved in TFE (7.8ml) and purged with argon at −10°. TFA (2.25ml, 30 mmoles, 22%) was added to the milky solution at −5°. The mixture immediately turned bright orange-red, then darkened while warming up to room temperature for 18.5 hours. 25ml of 10% aqueous potassium hydroxide was added slowly at 0°. At the neutralization point, a distinct color change from deep brown to light yellow could be noticed. After 15 minutes the mixture was worked up with ether in the usual way to give 41mg of a brown gum. The ir indicated that a small amount of trifluoroacetate(s) had not been hydrolyzed yet. The mixture was prepurified on 4g of Florisil. Hexane - ether 9:1 removed apolar nonidentified material. Hexane - ether 4:1 eluted 13mg of material which were further purified by preparative tlc (hexane - ethyl acetate 9:1, 3x) to give 7mg (17%) of the tetracyclic benzyl ether as an oil.

The following table provides a number of preparations with varying conditions.

TABLE I

| Run | Substrate μmol | molarity | TFA ml | mmol | TFE ml % | ml | Temp. | Time hr |
|---|---|---|---|---|---|---|---|---|
| 1 | 25 | 0,013 | 0,037 | 0,5 | 2 | 1,85 | 0° | 17 |
| 2 | 25 | 0,012 | 0,185 | 2,5 | 9 | 1,85 | 0° | 17 |
| 3* | 25 | 0,012 | 0,185 | 2,5 | 9 | 1,85 | 0° | 17 |
| 4 | 25 | 0,012 | 0,185 | 2,5 | 9 | 1,85 | 0° RT | 0,25 20,5 |
| 5 | 25 | 0,010 | 0,55 | 7,5 | 23 | 1,85 | 0° | .17 |
| 6 | 25 | 0,010 | 0,55 | 7,5 | 23 | 1,85 | 0° RT | 0,25 4 |
| 7 | 25 |  | 0,275 | 3,75 |  | 1,85 | 0° | .5 |
|  |  | 0,010 | 0,275 | 3,75 | 23 | 1,85 | 0° | 15 |
| 8 | 25 | 0,013 | 1,0 | 13,0 | 50 | 1,0 | 0° | 2 |
| 9 | 25 | 0,013 | 1,0 | 13,0 | 50 | 1,0 | 0° | 10 |
| 10 | 25 | 0,013 | 1,0 | 13,0 | 50 | 1,0 | 0° RT | 0,25 10 |

* = inverse addition

EXAMPLE 21

A-nor-11 α-Hydroxy-3-methyl-3-pregnen-20-one, 23a

A stirred solution of the cyclopentenone 15b (120mg, 0.4 mmoles) in anhydrous ether (20ml freshly distilled from LAH) was cooled to 0°. Methyllithium - ether (1.6 mmoles) was added dropwise under nitrogen. After 15 minutes the reaction was quenched by dropwise addition of ice-cold, wet ether (about 5ml) followed by some anhydrous potassium carbonate. A few minutes later, the cold suspension was filtered, and the drying agent was rinsed with several portions of dry ether. The combined filtrate was evaporated at 0°/9mm then further freed from solvent traces at 0°/0.5mm for about 10 minutes. The residue was redissolved in a total of 5.5ml of cold, argon-saturated TFE (milky solution) and transferred slowly via syringe into a well-stirred mixture of TFE (20ml) and TFA (7.5ml dist. from molecular sieves A3) which had been cooled to −10° and purged with argon for 10 minutes. The mixture turned cloudy. The color changed soon from bright yellow to deep brown-red. After being stirred under argon at room temperature for 40 hours the mixture was transferred via syringe into ice-cold 5M aqueous potassium hydroxide (30ml) whereby the intense color disappeared immediately. The mixture was thoroughly extracted with ether. The ether phase was washed with brine, dried over magnesium sulfate and evaporated. The residue which contained small amounts of unhydrolyzed trifluoroacetate(s) (ir: 5.60) was treated with 0.02ml of 15% aqueous potassium hydroxide in 2.0ml of methanol for 30 minutes. Usual workup with ether afforded 130mg of a brown gum.

The following table indicates a number of preparations with varying conditions.

TABLE II

| Run | Substrate mmol | Substrate molarity | TFA ml | TFA mmol | TFA ml% | TFE ml | Temp.+ | Time hr | Yield mg | Yield % |
|---|---|---|---|---|---|---|---|---|---|---|
| 1 | 0,20 | 0,01 | 4,4 | 58,7 | 22,0 | 15,6 | RT | 16 | 14 | 22 |
| 2 | 0,13 | 0,01 | 3,0 | 40,0 | 22,5 | 10,3 | 4° | 45 | 10 | 24 |
| 3 | 0,15 | 0,01 | 3,5 | 46,2 | 23,3 | 11,5 | RT | 40 | 13 | 27 |
| 4 | 0,15 | 0,01 | 5,0 | 66,5 | 33,3 | 10,0 | RT | 17,5 | 13,4 | 28 |
| 5* | 0,30 | 0,012 | 5,5 | 73,0 | 22,0 | 19,5 | RT | 34 | 32 | 34 |
| 6 | 0,40 | 0,015 | 7,5 | 100,0 | 25,0 | 22,5 | RT | 21 | 28 | 22 |
| 7* | 0,40 | 0,012 | 7,5 | 100,0 | 22,0 | 22,5 | RT | 40 | 45 | 35 |

\* = inverse addition
+ − RT = room temperature

EXAMPLE 22

A-nor-11 α-Acetoxy-3-methyl-pregnen-20-one

45mg (0.143 mmoles) of chromatographed alcohol 23a was dissolved in 0.4ml of acetic anhydride - pyridine 1:1 and allowed to stand at room temperature for 12 hours. 0.2ml of pyridine and 0.2ml of 85% lactic acid reagent were added. After 30 minutes the mixture was diluted with ether and washed with ice plus aqueous sodium bicarbonate, brine, aqueous cupric sulfate and brine. The organic layer was dried over magnesium sulfate and evaporated to give 49mg of crude acetate. The tlc showed several polar impurities besides the major spot. The material was combined with 30mg from an identical run and chromatographed on 16g of silica gel with hexane - ethyl acetate 4:1. 58mg (70%) of white crystals were obtained, mp 100°-106°.

EXAMPLE 23

(±) 11 α-Hydroxy-progesterone, 25a 39.6mg (0.11 mmoles) of the acetate (Ex. 22) in dichloromethane (1.0ml) was treated with 0.12 mmoles of ozone in 3.0ml of dichloromethane at −78° (Rubin ozonizer). After 5 minutes the excess of ozone was removed by a soft nitrogen stream. The colorless solution was warmed up to room temperature, then concentrated under reduced pressure. The residue was redissolved in dichloromethane - acetic acid 3:1 (3.2ml) and stirred in the presence of zinc powder (90mg) for 4 hours. The suspension was filtered. Usual workup of the filtrate with ether gave 44mg of crude trisketone 24a appearing as essentially one polar spot on tlc.

A solution of this compound in 5% methanolic potassium hydroxide (4ml purged with argon) was refluxed under nitrogen for 3 hours. Usual workup with ether afforded 34mg of a white foam which was chromatographed on a preparative plate with hexane - ethyl acetate - methanol 40:58:2 (seven elutions). The white, bulky crystals (17mg, 47%) which were obtained from the more polar band were recrystallized once from methanol to yield 11mg of (±) 11-α-hydroxy-progesterone, 25a.

MISCELLANEOUS COMPOUNDS

EXAMPLE 24 tert.-Butyldimethylsilyl ether

The alcohol 16b (15mg, 0.05 mmoles) in anhydrous dimethylformamide (distilled from calcium hydride, 60 ml) was treated with imidazole (8.2mg, 0.12 mmoles) and tert.-butyldimethylsilyl chloride (9mg, 0.06 mmoles). After one night at 35°-38°, a tlc of this mixture showed that only about 60-70% of the alcohol 16b had been converted to the silyl ether derivative. The reaction mixture was combined with a similar one, worked up as usual and purified by preparative tlc. Elution with hexane - ethyl acetate 1:1 afforded a sample of the silyl ether at C-11 as a slightly yellow oil.

EXAMPLE 25

Trimethylsilyl ether

Sodium hydride (57% dispersion in mineral oil, 3mg, 0.075 mmoles) was added to a solution of the alcohol 16b (15mg, 0.05 mmoles) in 0.3ml of anhydrous tetrahydrofuran. When the gas evolution had ceased (15 minutes), bis (trimethylsilyl) trifluoroacetamide (14μl, 0.05 mole) was added. After 30 minutes the mixture was diluted with ether and quickly washed with brine. The organic phase was dried over magnesium sulfate and evaporated. The residue had to be retreated in exactly the same manner in order to get complete conversion to the silyl ether at C-11.

It is evident from the prior examples, that in accordance with this invention, steroids can be easily synthesized with a wide variety of substituents at the 11-position. In addition, great flexibility is provided for introducing groups in the side chain at the 17-position and providing for nor-steroids, either at the 18 or 19-position or in the A-ring. Also, the chain length at the 18 and 19-positions may be varied. The central compound is a dienyne which may have a variety of groups which are functionalized, so that upon initation with an acid catalyst, the molecule cyclizes to the steroid cyclic structure or the A-nor-steroid cyclic structure. By appropriate choice of the Z group or by subsequent treatment, either the cholestane or coprostane geometry may be achieved.

The procedures employed for synthesizing the steroids introduce the proper geometry for double bonds, so that upon cyclization the natural steroid geometry is obtained. Cyclization of the polyunsaturated compound to the desired steroid product is achieved despite substantial non-bonded steric interactions which result as the molecule becomes compressed into the tetracyclic product. In addition, the acetylenic bond provides for 5-membered ring formation directly.

The cyclization is carried out in strong acid media and it is found that good yields of the steroid product can be obtained. The conditions employed are for more rigorous than the cyclization conditions for the polyenyne which is unsubstituted at the C-11 position. The C-11 chalcoxy substituted polyenynes are capable of cyclization with retention of the substituents which, if desired, may be modified to other functionalities. Thus, a direct route into C-ring functionalized compounds is provided, which may be used for the preparation of corticosteroids, analogues of the corticosteroids or other C-ring functionalized steroids.

Although the foregoing invention has been described in some detail by way of illustration and example for purposes of clarity of understanding, it will be obvious that certain changes and modifications may be practiced within the scope of the appended claims.

What is claimed is:

1. A compound of the formula:

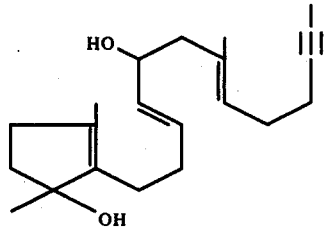

* * * * *